United States Patent [19]

Better et al.

[11] Patent Number: 5,276,243
[45] Date of Patent: Jan. 4, 1994

[54] SULFOLANE PURIFICATION METHOD

[75] Inventors: Michael A. Better, Deptford; Jonathan E. Child, Sewell; Kenneth J. Del Rossi, Woodbury; Anagha A. Gupte, Marlton; Tomas R. Melli, Sewell, all of N.J.; Sergei Yurchak, Media, Pa.

[73] Assignee: Mobil Oil Corporation, Fairfax, Va.

[21] Appl. No.: 991,922

[22] Filed: Dec. 17, 1992

Related U.S. Application Data

[63] Continuation-in-part of Ser. No. 833,684, Feb. 11, 1992, Pat. No. 5,191,150.

[51] Int. Cl.⁵ .......................... C07C 2/62; C07C 7/10
[52] U.S. Cl. ................................. 585/802; 585/723; 585/724; 585/857
[58] Field of Search ............... 585/724, 723, 802, 857

[56] References Cited

U.S. PATENT DOCUMENTS

| | | | |
|---|---|---|---|
| 3,795,712 | 3/1974 | Torck et al. | 585/724 |
| 4,014,953 | 3/1977 | Brown, Jr. | 585/724 |
| 4,058,575 | 11/1977 | Cahn et al. | 585/724 |
| 4,199,409 | 4/1980 | Skraba | 585/724 |
| 4,317,795 | 3/1982 | Makovec et al. | 422/62 |
| 4,663,026 | 5/1987 | Louie et al. | 585/723 |
| 5,191,150 | 3/1993 | Child et al. | 585/809 |

Primary Examiner—Asok Pal
Attorney, Agent, or Firm—Alexander J. McKillop; Dennis P. Santini; Robert B. Furr, Jr.

[57] ABSTRACT

The present invention provides a method for separating conjunct polymers and sulfolane from a mixture containing conjunct polymers, sulfolane, and hydrofluoric acid comprising the sequential steps of:
(a) separating hydrofluoric acid from said mixture to provide an intermediate stream containing less than about 30 percent hydrofluoric acid by weight;
(b) gravitationally separating said intermediate stream into a sulfolane-enriched stream and a conjunct polymer-enriched stream;
(c) contacting said sulfolane-enriched stream with a polar extraction solvent to provide an extract stream enriched in sulfolane and a raffinate stream enriched in conjunct polymers;
(d) stripping the polar extraction solvent from said sulfolane-enriched extract stream; and
(e) recovering sulfolane from said enriched stream of step (d).

15 Claims, 1 Drawing Sheet

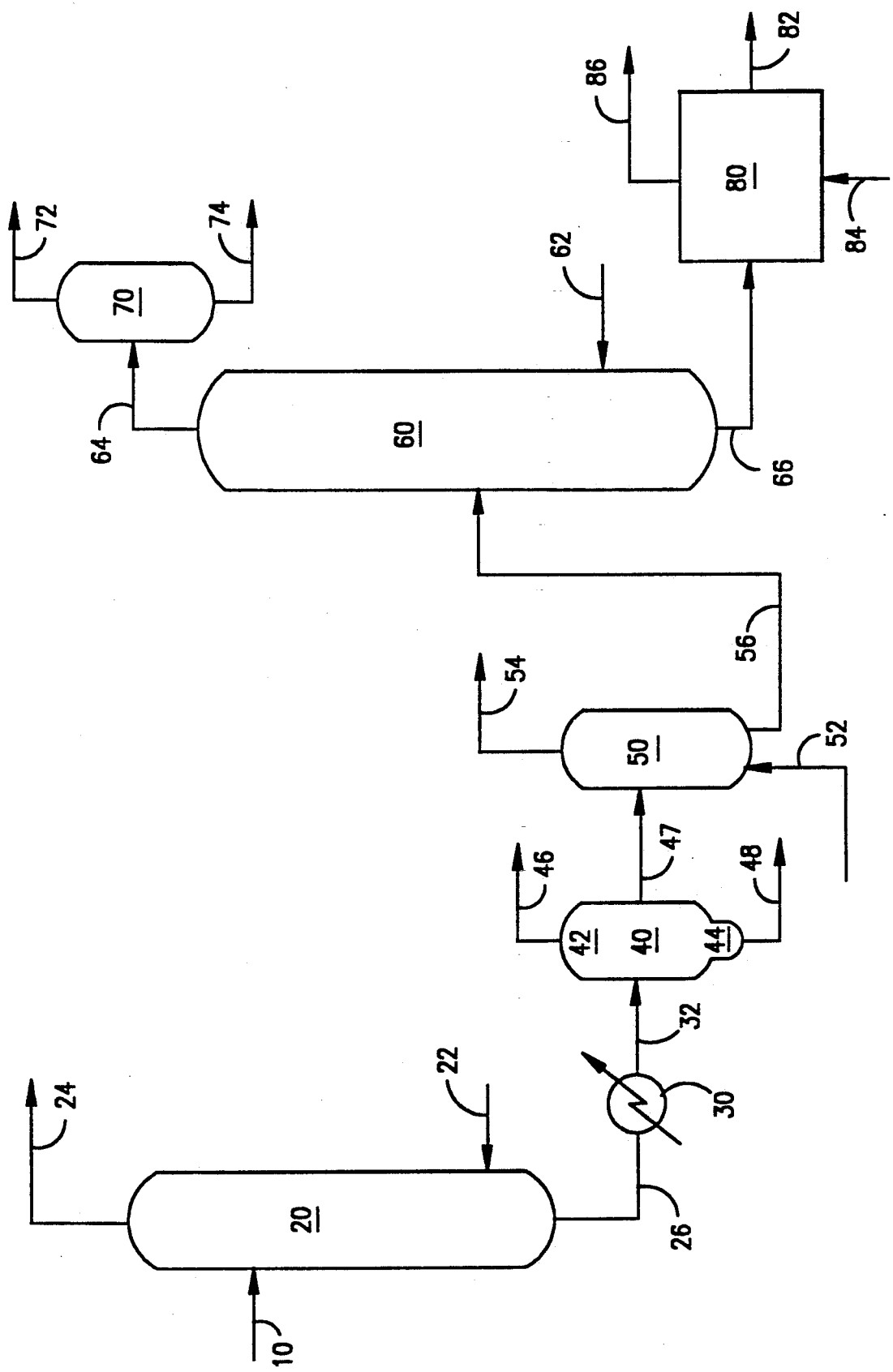

SULFOLANE PURIFICATION METHOD

CROSS REFERENCE TO RELATED APPLICATIONS

This is a continuation-in-part or application Ser. No. 07/833,684, filed Feb. 11, 1992, now U.S. Pat. No. 5,191,150. This application is related by disclosure of similar subject matter to Ser. No. 07/991,918, filed Dec. 17, 1992, Ser. No. 07/991,919, filed Dec. 17, 1992, Ser. No. 07/991,920, filed Dec. 17, 1992, and Ser. No. 07/991,921, filed Dec. 17, 1992, filed on even date herewith now all allowed.

FIELD OF THE INVENTION

The present invention relates to the art of catalytic alkylation. More specifically, the invention relates to a liquid alkylation catalyst and an isoparaffin-olefin alkylation process. Particularly, the invention provides a liquid alkylation catalyst composition which avoids many of the safety and environmental concerns associated with concentrated hydrofluoric acid.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used concentrated hydrofluoric or sulfuric acid catalysts under relatively low temperature conditions. Acid strength is preferably maintained at 88 to 94 weight percent by the continuous addition of fresh acid and the continuous withdrawal of spent acid. As used herein, the term "concentrated hydrofluoric acid" refers to an essentially anhydrous liquid containing at least about 85 weight percent HF.

Hydrofluoric and sulfuric acid alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381–397, (1988). For a survey of hydrofluoric acid catalyzed alkylation, see 1 *Handbook of Petroleum Refining Processes* 23-28 (R. A. Meyers, ed., 1986).

Hydrogen fluoride, or hydrofluoric acid (HF) is highly toxic and corrosive. However, it is used as a catalyst in isomerization, condensation, polymerization and hydrolysis reactions. The petroleum industry used anhydrous hydrogen fluoride primarily as a liquid catalyst for alkylation of olefinic hydrocarbons to produce alkylate for increasing the octane number of gasoline. Years of experience in its manufacture and use have shown that HF can be handled safely, provided the hazards are recognized and precautions taken. Though many safety precautions are taken to prevent leaks, massive or catastrophic leaks are feared primarily because the anhydrous acid will fume on escape creating a vapor cloud that can be spread for some distance. Previous workers in this field approached this problem from the standpoint of containing or neutralizing the HF cloud after its release.

U.S. Pat. Nos. 4,938,935 and 4,985,220 to Audeh and Greco, as well as U.S. Pat. No. 4,938,936 to Yan teach various methods for containing and/or neutralizing HF acid clouds following accidental releases.

But it would be particularly desirable to provide an additive which decreases the cloud forming tendency of HF without compromising its activity as an isoparaffin-olefin alkylation catalyst. Solvents and complexing agents for hydrofluoric acid have, in the past, been disclosed for various purposes as noted in the following references.

U.S. Pat. No. 2,615,908 to McCaulay teaches thioether-HF-copper complex compounds and a method for preparing the same. Potential uses for the thioether-HF-copper composition compounds are listed from column 6, line 55 through column 8 at line 3. The method is said to be useful for purifying HF-containing vent gases from an industrial HF alkylation plant. See column 7, lines 10-24.

U.S. Pat. No. 3,531,546 to Hervert discloses a HF-$CO_2$ catalyst composition which is said to be useful for alkylation as well as olefin isomerization.

U.S. Pat. No. 3,795,712 to Torck et al. relates to acid catalysts comprising a Lewis acid, a Bronsted acid, and a sulfone of the formula $R$—$SO_2$—$R'$, where R and R' are each separately a monovalent radical containing from 1 to 8 carbon atoms or form together a divalent radical having from 3 to 12 carbon atoms.

U.S. Pat. No. 3,856,764 to Throckmorton et al. teaches an olefin polymerization catalyst comprising (1) at least one organoaluminum compound, (2) at least one nickel compound selected from the class consisting of nickel salts of carboxylic acids, organic complex compounds of nickel, or nickel tetracarbonyl and (3) at least one hydrogen fluoride complex prepared by complexing hydrogen fluoride with a member of the class consisting of ketones, ethers, esters, alcohols, nitriles, and water.

U.S. Pat. Nos. 4,025,577 and 4,099,924 to Siskin et al. report the use of alkylation catalyst compositions containing HF, a metal halide, and sulfolane. U.S. Patent to Olah relates to an additive formulation which reduces the fuming tendency of HF.

Promoters such as alcohols, thiols, water, ethers, thioethers, sulfonic acids, and carboxylic acids are disclosed in combination with strong Bronsted acids such as HF, fluorosulfonic and trihalomethanesulfonic acids in U.S. Pat. No. 3,778,489 to Parker et al. The promoters are said to modify the activity of the strong Bronsted acids for alkylation.

The preceding references demonstrate the desirability of a liquid Bronsted acid catalyst (such as HF) for isoparaffin-olefin alkylation, as well the utility of liquid Bronsted acids in combination with metal halides, particularly metal fluorides.

In U.S. application Ser. No. 07/719,879, filed Jun. 21, 1991, now abandoned, an isoparaffin-olefin alkylation process is disclosed which uses an HF/sulfolane catalyst containing relatively high concentrations of sulfolane, and is incorporated by reference for the details of isoparaffin-olefin alkylation with a sulfolane-enriched HF catalyst.

SUMMARY OF THE INVENTION

The present invention provides a method for separating conjunct polymers and sulfolane from a mixture containing conjunct polymers, sulfolane, and hydrofluoric acid. In a first embodiment, the invention comprises the steps of:

(a) separating hydrofluoric acid from said mixture to provide an intermediate stream containing less than about 30 percent hydrofluoric acid by weight;

(b) gravitationally separating said intermediate stream into a sulfolane-enriched stream and a conjunct polymer-enriched stream;

(c) contacting said sulfolane-enriched stream with a polar extraction solvent to provide an extract stream enriched in said polar solvent and sulfolane and a raffinate stream enriched in conjunct polymers;

(d) stripping said polar extraction solvent from said extract stream to provide a stream enriched in sulfolane; and (e) recovering sulfolane from said enriched stream of step (d).

The method finds particular utility in regenerating an HF/sulfolane catalyst used in an isoparaffin-olefin alkylation process. The hydrofluoric acid concentration of the catalyst mixture must be decreased prior to the gravitational separation step, preferably by stripping. While any suitable inert stripping fluid may be employed, a normal paraffin (e.g., n-butane), or isoparaffin (e.g., isobutane), is preferred. An isoparaffin suitable for isoparaffin-olefin alkylation (such as isobutane) is still more preferred. Alkylate formed by the reaction of an isoparaffin with an olefin may also be vaporized and effectively used as a stripping fluid.

Two sequential stripping steps may be used, as the sulfolane/conjunct polymer phases appear to separate more completely as the hydrofluoric acid concentration is decreased. If two-stage stripping is used, the second stripping fluid may comprise a hydrocarbon gas (such as isobutane or normal butane) or a non-hydrocarbon gas (such as nitrogen).

The effects of stripping hydrofluoric acid from the mixture before gravitational separation become particularly evident as the mixture is stripped to hydrofluoric acid levels of less than about 30 weight percent. Separation improves as the hydrofluoric acid content is decreased, with intermediate stream hydrofluoric acid concentrations preferably falling below 25 percent by weight, more preferably below about 10 percent hydrofluoric acid by weight, and most preferably below about 5 percent by weight.

The present process comprises the sequential steps of stripping, gravitational separation, and solvent extraction to purify and recover sulfolane for recycle to the alkylation process unit. After the HF/sulfolane/water mixture is stripped to 30 weight percent or less of HF, the stripped mixture is charged to a gravitational separation zone. Solids, sludge, and high density organics are drawn off as the most dense bottom layer, but, because the volume of this phase is typically quite small in comparison with the other two phases, the gravitational separation zone can be effectively operated as a two-phase gravitational separation with a bottom solids draw-off. The upper (less dense) liquid phase formed in the first gravitational separation step is enriched in conjunct polymeric byproducts (acid soluble oil or ASO) and may be processed to recover residual sulfolane or may be processed for disposal, depending upon the concentration of recoverable residual sulfolane.

The lower (more dense) liquid phase withdrawn from the gravitational separation step (which contains HF, sulfolane, ASO, and water, and which is enriched in sulfolane) is then contacted with a polar extraction solvent. The term "polar extraction solvent" as used herein refers to solvents in which the positive and negative charges are permanently separated. Generally, the polar extraction solvent should have a high affinity for sulfolane and a low affinity for ASO. Polar solvents useful in the present invention include solvents having a dipole moment ($\mu$) of at least about 0.6 debyes, examples of which include water, as well as organics containing carboxyl or hydroxyl groups, such as alcohols and carboxylic acids. Specific examples of useful alcohols include ethanol ($\mu=1.69$), 1-propanol ($\mu=1.68$), and 2-propanol ($\mu=1.66$). Useful carboxylic acids include formic acid ($\mu=1.41$) and acetic acid ($\mu=1.74$). Water ($\mu=1.84$) is a particularly preferred polar solvent.

The extraction solvent dosage may vary over a wide range depending upon operating conditions and the number of extraction stages, but typically ranges from about 0.1 to about 2.0 mass units of solvent per mass unit of feed, preferably from about 0.1 to about 0.7 mass units of solvent per mass unit of feed.

The extraction zone for contacting the extraction solvent with the sulfolane-enriched stream may comprise as many extraction stages as is economically feasible, typically from about 1 to about 10 theoretical stages, and preferably from about 2 to about 4 theoretical stages.

The extraction steps may be carried out in any suitable apparatus. If the polar extraction solvent is denser than sulfolane (density=1.26 g/cc) the extraction step may be carried out in a tower containing perforated trays and/or at least one packed bed containing contact materials such as Berl saddles, Raschig rings, or the like. If, on the other hand, the solvent density is less than 1.26 g/cc, it is preferable to conduct the extraction step in a train of mixer-settlers. The mixer-settlers may comprise stirred tanks or static mixers with downstream settling tanks. The mixer-settlers may be operated in either the countercurrent or the crosscurrent mode, but are generally more effective in the countercurrent mode.

The extract stream withdrawn from the extraction step, enriched in sulfolane, flows to a drying section which typically comprises at least one stripper and alternatively comprises a stripper together with a molecular sieve sulfolane drier. Useful drying agents include activated alumina, activated carbon, and acid-resistant sieves such as Zeolon molecular sieves (manufactured by Nerton Co. Chemical and Products Division).

Operating temperatures for the sulfolane extraction step typically range from about 30° F. to about 200° F., with temperatures of from about 50° F. to about 120° F. providing improved extraction performance.

BRIEF DESCRIPTION OF THE DRAWINGS

The Figure is a simplified schematic diagram showing major processing steps in the method of the invention.

EMBODIMENTS

Referring now to the Figure, a slipstream of spent alkylation catalyst 10 flows from an operating HF/sulfolane catalyzed isoparaffin-olefin alkylation process unit (not shown) and enters distillation/stripping tower 20. Stripping gas, for example, isobutane, enters distillation/stripping tower 20 through line 22, carries stripped HF upwardly through the tower, and exits the distillation/stripping tower 20 via overhead line 24. The HF-enriched isobutane may optionally be fractionated again, but is preferably charged directly back to the isoparaffin-olefin alkylation process unit (not shown). The distillation/stripping tower bottoms product is charged through line 26 at tower temperature of about 300° F. ($\approx$149° C.) and flows to cooler 30. The bottoms product, cooled to about 70° F. ($\approx$21° C.), flows through line 32 and enters gravitational separator 40 at approximately atmospheric pressure.

Two liquid phases form within gravitational separator 40. The upper, less dense phase, enriched in ASO, collects near the top 42 of gravitational separator 40, and is withdrawn through line 46 for further processing, for example, neutralization and disposal or additional sulfolane recovery. Solids and the most dense residual hydrocarbons collect in a bottom boot 44, and are similarly withdrawn for further processing through line 48. The lower, less dense liquid phase, enriched in sulfolane, flows out of gravitational separator 40 through line 47 and enters extractor 50, which operates at about ambient temperature and pressure. Process water enters extraction column 50 near the bottom through line 52 and selectively dissolves the sulfolane. The extract stream then flows out of extractor 50 through line 56.

The extract stream from extractor 50, principally containing water and sulfolane, flows through line 56 and enters water stripping column 60 on a middle tray. Isobutane enters stripping column 60 near the bottom through line 62. The isobutane becomes enriched in water as it rises through the column and is withdrawn from stripping column 60 through line 64. Isobutane and water flow out of stripping column 60 through line 64 and enter accumulator drum 70 where the isobutane and water are separated by gravity and the isobutane is withdrawn overhead through line 72. Water is drawn of through line 74.

The stripped sulfolane then flows through line 66 to molecular sieve drier 80 and is finally recycled to the alkylation process unit (not shown) via line 82. The molecular sieve drier operates in a parallel/swing mode such that one bank of driers is on-line while a second bank is being regenerated. During regeneration, a dry inert gas such as isobutane flows through line 84 at a temperature of about 450° F. desorbing water from the molecular sieve. The wet regeneration gas is withdrawn through line 86 and flows to a separator (not shown) or other drier before it is recycled to the alkylation process unit or recycled for use as a stripping fluid in stripping tower 60 or distillation/stripping tower 20. The molecular sieve drier 80 is optional and the process operates effectively with or without this drier.

COMPARATIVE EXAMPLE

A mixture of hydrofluoric acid, sulfolane, and conjunct polymeric byproducts (which conjunct polymeric byproducts are evolved from the catalytic alkylation of isobutane with butene, referred to hereinafter as acid soluble oil or ASO) containing about 65 weight percent hydrofluoric acid, 30 weight percent sulfolane and about 5 weight percent ASO, is charged to a decantation vessel at ambient temperature and pressure sufficient to maintain the mixture in the liquid phase. The mixture is allowed to stand for approximately 24 hours. No phase separation is observed.

EXAMPLE 1

A mixture of hydrofluoric acid, sulfolane, and ASO (having the same composition as the mixture of the Comparative Example, above) is charged to a stripping tower having three theoretical stages. Isobutane is introduced into the tower at a level below the height of the liquid (HF/sulfolane/ASO) charge point, and the isobutane and mixture charge rates are controlled to maximize stripping of HF while operating below the flooding point of the tower. A stripped liquid is withdrawn from the bottom of the tower and a HF-enriched isobutane stream is withdrawn from the top of the tower. The stripped liquid contains less than about 30 percent by weight of hydrofluoric acid.

The stripped liquid is then charged to a decantation vessel and allowed to stand for approximately 24 hours. The mixture separates into two distinct phases, an upper, less dense ASO-enriched phase, and a lower, more dense, sulfolane-enriched phase.

EXAMPLES 2-4

Additional samples of the mixture of hydrofluoric acid, sulfolane, and ASO (having the same composition as the mixture of the Comparative Example) are stripped with isobutane to hydrofluoric acid contents of 25 weight percent, 10 weight percent, and 5 weight percent, respectively. The stripped mixtures containing lower concentrations of hydrofluoric acid separate into two phases with higher purity. The ASO concentration in the sulfolane phase and the sulfolane in the ASO phases decreases as the HF concentration in the stripper bottoms decreases.

EXAMPLE 5

The HF/sulfolane sample of Example 5 has the following composition:

| | |
|---|---|
| HF | 62 wt. % |
| Sulfolane | 27 wt. % |
| Isobutane | 4 wt. % |
| Water | 1-2 wt. % |
| ASO | 3 wt. % |
| Balance to 100% other hydrocarbons. | |

This mixture is a single liquid phase at 90° F. and 120 psig.

The sample is brought to atmospheric pressure and room temperature and most of the light hydrocarbons and part of the HF are vented off. Under these conditions, the sample is a single liquid phase containing about 50 wt. % HF.

Nitrogen is then bubbled through the mixture at room temperature and atmospheric pressure to strip HF off the mixture. As the mixture is depleted in HF, the mixture separates into two phases. In Example 5, the two phases appear within several minutes of the HF concentration reaching about 2 wt. %.

Both phases are analyzed, and the dense phase (specific gravity about 1.26) contains 83.2 wt. % sulfolane, 2.2 wt. % ASO, and the balance water, salts, and a sludge. The lighter phase, having a density of less than about 1, contains 82.8 wt. % ASO, 13.3 wt. % sulfolane, and the balance of salts.

EXAMPLE 6

A mixture of isobutane and 2-butene is contacted with an alkylation catalyst comprising 65.6% HF, 32.4% sulfolane and 2% water by weight in a riser reactor. The catalyst is analyzed after the process reaches substantially steady state and is found to contain the following:

62.8 wt. % HF
31 wt. % sulfolane
1.8 wt. % water
4.4 wt. % ASO

The HF content is then decreased to 22.7% HF by stripping with nitrogen. The resulting stripped catalyst is extracted with water (water: catalyst ratio=0.5 by weight). The mixture is agitated and separated into two phases: an extract phase enriched in water and sulfolane, and a raffinate phase enriched in ASO. The ASO phase contained 10.4% sulfolane by weight. The sulfolane-rich phase contained only 3.05% by weight ASO on an HF— and water-free basis showing an 88.9% removal of ASO from the catalyst.

Changes and modifications in the specifically described embodiments can be carried out without departing from the scope of the invention which is intended to be limited only by the scope of the appended claims.

What is claimed is:

1. A method for separating conjunct polymers and sulfolane from a mixture containing conjunct polymers, sulfolane, and hydrofluoric acid comprising the sequential steps of:
    (a) separating hydrofluoric acid from said mixture to provide an intermediate stream containing less than about 30 percent hydrofluoric acid by weight;
    (b) gravitationally separating said intermediate stream into a sulfolane-enriched stream and a conjunct polymer-enriched stream;
    (c) contacting said sulfolane-enriched stream with a polar extraction solvent to provide an extract stream enriched in sulfolane and a raffinate stream enriched in conjunct polymers;
    (d) stripping the polar extraction solvent from said sulfolane-enriched extract stream; and
    (e) recovering sulfolane from said enriched stream of step (d).

2. The method of claim 1 wherein said conjunct polymers are formed as byproduct in an isoparaffin-olefin alkylation process.

3. The method of claim 1 wherein step (d) comprises contacting said sulfolane-enriched extract with a stripping fluid.

4. The method of claim 3 wherein said stripping fluid comprises at least one selected from the group consisting of isoparaffins and normal paraffins.

5. The method of claim 4 wherein said stripping fluid is selected from the group consisting of isobutane and normal butane.

6. The method of claim 3 wherein said stripping fluid comprises the alkylate product formed by reacting an isoparaffin with an olefin.

7. The method of claim 3 wherein step (d) comprises stripping said sulfolane-enriched extract stream with isobutane.

8. The method of claim 3 wherein said stripping step comprises sequentially stripping said mixture with isoparaffin and then stripping said mixture with nitrogen.

9. The method of claim 1 wherein said hydrofluoric acid separation step provides an intermediate stream containing less than about 25 percent hydrofluoric acid by weight.

10. The method of claim 9 wherein said hydrofluoric acid separation step provides an intermediate stream containing less than about 10 percent hydrofluoric acid by weight.

11. The method of claim 10 wherein said hydrofluoric acid separation step provides an intermediate stream containing less than about 5 percent hydrofluoric acid by weight.

12. The method of claim 1 wherein said polar extraction solvent has a dipole moment of at least about 0.6 debyes.

13. The method of claim 1 wherein said polar solvent contains at least one hydroxyl or carboxyl group.

14. The method of claim 13 wherein said polar extraction solvent is selected from the group consisting of alcohols and carboxylic acids.

15. The method of claim 12 wherein said polar extraction solvent is water.

* * * * *